United States Patent [19]

Sarges et al.

[11] 4,210,667

[45] Jul. 1, 1980

[54] PHARMACEUTICAL PREPARATIONS CONTAINING COUMARIN CARBOXYLIC ACID DERIVATIVES

[75] Inventors: Reinhard Sarges, Mystic, Conn.; John L. Belletire, Madison, Wis.; Rodney C. Schnur, Noank, Conn.

[73] Assignee: Pfizer Inc., New York, N.Y.

[21] Appl. No.: 31,564

[22] Filed: Apr. 19, 1979

[51] Int. Cl.² .............................................. A61K 31/37
[52] U.S. Cl. .................................................... 424/281
[58] Field of Search ........................................ 424/281

[56] References Cited

U.S. PATENT DOCUMENTS

| 3,821,383 | 6/1974 | Sestanj et al. | 424/258 |
| 3,975,535 | 8/1976 | Buckle et al. | 424/279 |
| 4,117,230 | 9/1978 | Sarges | 548/309 |
| 4,127,665 | 11/1978 | Sarges et al. | 424/273 |
| 4,130,714 | 12/1978 | Sarges | 548/309 |

Primary Examiner—Frederick E. Waddell
Attorney, Agent, or Firm—F. X. Murphy; C. J. Knuth; A. J. Nelson

[57] ABSTRACT

Preparations useful as aldose reductase inhibitors and as therapeutic agents for the treatment of chronic diabetic complications are disclosed. The preparations contain substituted and unsubstituted coumarin-4-carboxylic or acetic acid derivatives as the active ingredients.

9 Claims, No Drawings

PHARMACEUTICAL PREPARATIONS CONTAINING COUMARIN CARBOXYLIC ACID DERIVATIVES

BACKGROUND OF THE INVENTION

This invention relates to novel pharmaceutical preparations containing coumarin carboxylic acid derivatives which are useful in the treatment of certain chronic complications arising from diabetes mellitus, such as diabetic cataracts and neuropathy.

Although many oral antidiabetic agents, such as the sulfonyl ureas, effectively lower blood sugar levels, the prevention or alleviation of the chronic complications of diabetes, such as diabetic cataracts, neuropathy, retinopathy and nephropathy has proved harder to achieve. According to the U.S. Pat. No. 3,821,383, aldose reductase inhibitors such as 1,3-dioxo-1H-benz[-d,e]-isoquinoline-2(3H)-acetic acid and its derivatives are useful in this regard. Spiro-hydantoin or imidazolidinedione compounds are also aldose reductase inhibitors and are described in U.S. Pat. No. 4,117,230, U.S. Pat. No. 4,130,714 and U.S. Pat. No. 4,127,665. Such compounds inhibit the enzymatic reduction of aldoses, such as glucose and galactose, to the corresponding polyols, such as sorbitol and galactitol, thus preventing or reducing the harmful and unwanted accumulations of polyols in the diseased organs of the body; for example, inhibition of glucose reduction would prevent sorbitol accumulation in the lens and retina of the diabetically cataractous eye, in the diabetically neuropathic peripheral nerve and in the diabetically nephropathic kidney.

SUMMARY OF THE INVENTION

The pharmaceutical preparations of the present invention will inhibit harmful, in vivo enzymatic reduction of aldoses or will prevent or alleviate related diabetes-associated complications. The preparations are combinations of pharmaceutically acceptable carriers and coumarin carboxylic acid derivatives of formulas I and II:

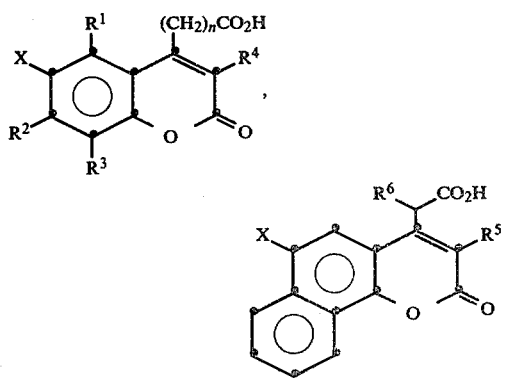

and the pharmaceutically acceptable salts thereof wherein $R^1$, $R^2$, $R^3$, $R^4$, $R^5$ and $R^6$ are independently selected from H or $CH_3$; X is H, $CH_3$, F or Cl; and n is 0 or 1; provided that when $R^1$ is $CH_3$, $R^2$ or $R^3$ is $CH_3$.

Preferred embodiments include the preparations containing:
the derivative of formula I wherein $R^1$ and $R^3$ are H; $R^2$, $R^4$ and X are $CH_3$; and n is 1;
the derivative of formula I wherein X, $R^3$ and $R^4$ are H, $R^1$ and $R^2$ are $CH_3$ and n is 1;
the derivative of formula I wherein $R^1$, $R^3$, $R^4$ and X are H; $R^2$ is $CH_3$; and n is 1;
the derivative of formula I wherein $R^1$, $R^3$ and $R^4$ are H; $R^2$ and X are $CH_3$; and n is 1;
the derivative of formula I wherein $R^1$, $R^2$ and $R^4$ are H; $R^3$ is $CH_3$; X is Cl; and n is 0;
the derivative of formula II wherein $R^5$ and $R^6$ are H; and X is Cl; and
a mixture of the derivatives of formula II wherein $R^5$ is H; $R^6$ is $CH_3$; and X is Cl and wherein $R^6$ is H; $R^5$ is $CH_3$; and X is Cl.

The invention also includes a method of inhibiting harmful, in vivo enzymatic reduction of aldoses and a related method of preventing or alleviating diabetes-associated complications, which involve administering a therapeutic amount of a coumarin carboxylic acid derivative.

DETAILED DESCRIPTION OF THE INVENTION

The derivatives are the active ingredients of the preparations of the invention and are known or may be easily prepared by condensing an acetonedicarboxylic acid or ketosuccinic acid with the appropriate phenol compound. This is the well-known Pechmann reaction, Ber. 16, 2119 (1883). Sethna and Phadke review the scope of the reaction in Org. Reactions 7, 1-58 (1953) and several procedures are provided in Organic Synthesis, col. Vol. III and IV, John Wiley & Sons, New York. Examples are also given below.

The pharmaceutically acceptable salts of the derivatives can readily be prepared using conventional methods. Aqueous neutralization of the derivative with an appropriate, pharmaceutically acceptable amine or metallic or ammonium hydroxide and evaporation of the water, preferably under reduced pressure, will afford the salt. Alternatively, a lower alkanol solvent and an appropriate amine or a metallic lower alkoxide may be used. Suitable metallic cations include alkaline or alkaline earth metals and the common pharmaceutically acceptable transition metals. Suitable amines include mono, di and tri lower alkyl amines, aryl and arylalkyl amines, heteroaromatic amines, aminoalcohols and the like.

The pharmaceutical preparations are of therapeutic value in the prophylactic and remedial treatment of chronic complications of diabetes, such as cataracts, retinopathy, nephropathy and neuropathy and of harmful, in vivo enzymatic reduction of aldoses associated with diabetes, galactosemia, and the like. They may be administered to a subject in need of treatment by a variety of conventional routes of administration, such as oral, intravenous, intramuscular, subcutaneous, topical, opthalmic as drops to the eye and intraperitoneal. In general, they will contain a dose of the coumarin carboxylic acid derivative of between 1 and 250 mg per kg body weight of the subject to be treated per day. However, the particular dose, formulation and route of administration depend upon each patient's unique condition and the judgment of his attending physician.

Methods of formulating the pharmaceutical preparations are well-known in the pharmacy art. In general the pharmaceutical preparations are combinations of the derivatives and pharmaceutically acceptable carriers such as inert solid diluents, aqueous solutions or various non-toxic organic solvents in dosage forms such as gelatin capsules, tablets, powders, lozenges, syrups, injectable solutions and the like. The carriers include water, ethanol, gelatins, lactose, starches, vegetable oils, petroleum jelly, gums, glycols, talc, benzyl alcohols and other known ingredients for medicaments. If desired, these pharmaceutical preparations may contain auxiliary material such as preserving agents, wetting agents, stabilizing agents, lubricating agents, absorption agents, buffering agents and isotonic agents. Examples are given below.

The ability of the active ingredients of the preparations, the derivatives, to control chronic diabetic complications and enzymatic reduction of aldoses may be determined by a number of standard biological or pharmacological tests. These include (1) measuring the ability to inhibit the enzyme activity or isolated aldose reductase; (2) measuring the ability to reduce or inhibit sorbitol accumulation in the sciatic nerve of acutely streptozotocinized (i.e., diabetic) rats; (3) measuring the ability to reverse already-elevated sorbitol levels in the sciatic nerve and lens of chronic streptozocin-induced diabetic rats; (4) measuring the ability to prevent or inhibit galactitol formation in the lens of acutely galactosemic rats; and (5) measuring the ability to delay cataract formation and reduce the severity of lens opacities in chronic galactosemic rats.

The following examples illustrate the synthesis of several derivatives, the formation of several pharmaceutical preparations and the biological activities of several derivatives in tests 1 and 2 above. It will be understood, however, that the invention is not limited to the specific details given.

General Procedure for Synthesis of Coumarin Carboxylic Acid Derivatives

The derivatives exemplified in Table 1 were prepared from the appropriate phenol compound and the appropriate beta ketoacid (acetonedicarboxylic or ketosuccinic acid derivative) using the following general procedure.

The coumarin carboxylic acid derivative was synthesized by stirring at ambient temperature for 24 to 72 hours, a solution of 0.2 to 0.3 m of the phenol compound, about 0.2 m of the beta ketoacid and about 100 to 250 ml of a Lewis acid such as concentrated sulfuric acid or boron trifluoride etherate in ether. The derivative was then worked up by pouring the solution over about 200 g ice and filtering the precipitated solid or if an aqueous solution resulted, extracting with ethyl acetate, drying the organic layer, filtering and removing the solvent in vacuo to afford the crude, solid product. It was purified by recrystallization from ethanol, isopropyl alcohol in hexanes or dimethylformamide.

The derivatives prepared, their melting points and their starting materials are listed in Table 1.

Table 1

| Ex. No. | Derivative | m.p. | phenol | beta ketoacid |
|---|---|---|---|---|
| 1* | 3,6,7-trimethyl-coumarin-4-acetic acid | 196°–198° C. | 3,4-xylenol | 1,3-acetone dicarboxylic acid |
| 2 | 6-chloro-1:2-alpha-naphthapyrone-4-acetic acid | 225°–6° C. | 4-chloro-1-naphthol | same as above |
| 3 | 5,7-dimethyl-coumarin-4-acetic acid | 182°–3.5° C. | 3,5-xylenol | same as above |
| 4 | 7-methylcoumarin-4-acetic acid | 203°–5° C. | m-cresol | diethyl 1,3-acetone dicarboxylate |
| 5 | 6,7-dimethyl-coumarin-4-acetic acid | 204°–6° C. | 3,4-xylenol | same as above |
| 6 | 6-chloro-8-methyl-coumarin-4-carboxylic acid | 229°–31° C. | 4-chloro-o-cresol | diethyl ketosuccinate sodium salt |
| 7* | mixture of 3-methyl-6-chloro-1:2-alpha-naphthapyrone-4-acetic acid and (6-chloro-1:2-alpha-naphthapyrone-4-)2-propionic acid | — | 4-chloro-1-naphthol | 1,3-acetone dicarboxylic acid |

| Example No. | Literature References |
|---|---|
| 2 | J. Ind. Chem. Soc., 13, 649 (1956) |
| 4 | Annalen, 379, 107 (1911) |
| 6 | J. Chem. Soc., 107, 1639 (1915) |

* These methylated derivatives were prepared from the corresponding normethyl derivatives which the condensation reaction produced. The reaction used, methylation of the coumarin enolate anion, involves well-known procedures. For example, preparation of the derivative of Example 1 is as follows: 3,4-xylenol and 1,3-acetonedicarboxylic acid were condensed to form 6,7-dimethylcoumarin-4-acetic acid. It was esterified with ethanol to form the ethyl ester. The ester was then reacted with sodium hydride in tetrahydrofuran and the sodium salt methylated with methyl iodide to form ethyl (6,7-trimethylcoumarin-4-)2-propionate. The propionate was heated for 24 to 98 hours at 50°–70° C. in 3N aqueous potassium hydroxide to hydrolyze and rearrange it to the derivative of Example 1.

Pharmaceutical Preparations

The following procedures provide methods of formulating pharmaceutical tablet, capsule and suspension preparations containing derivatives selected from the examples above.

Tablet

A tablet base is prepared by blending the following ingredients in the proportion by weight indicated:
Sucrose, U.S.P: 80.3
Tapioca starch: 13.2
Magnesium stearate: 6.5

Sufficient amounts of 3,6,7-trimethylcoumarin-4-acetic acid are blended into the tablet base to provide doses of 1.0, 50, 100 and 250 mg of active ingredient per tablet. These dosage forms are compressed into tablets, each weighing 500 mg, by convenient means.

Capsule

A blend is prepared containing the following ingredients:
Calcium carbonate, U.S.P: 17.6
Dicalcium phosphate: 18.8
Magnesium trisilicate, U.S.P: 5.2
Lactose, U.S.P: 5.2
Potato starch: 5.2
Magnesium stearate: 0.8

A second portion of magnesium stearate (0.35 g) and sufficient amounts of 6-chloro-1:2-alphanaphthapyrone-4-acetic acid are added to the blend to provide capsules containing 1.0, 50, 100 and 250 mg of active ingredient per capsule. The dosage forms are filled into conventional hard gelatin capsules in the amount of 500 mg per capsule.

Suspension

A suspension of 6,7-dimethylcoumarin-4-acetic acid and carrier ingredients is prepared as follows:
Active ingredient: g. 25.00

70% aqueous sorbitol: g. 741.29
Glycerine, U.S.P: g. 185.35
Gum acacia (10% solution): ml. 100.00
Polyvinylpyrrolidone: g. 0.50
Distilled water, sufficient to make 1 liter.

To this suspension, various sweeteners and flavorants are added to improve the palatability of the suspension. The suspension contains approximately 25 mg of active ingredient per milliliter.

Aldose Reductase Inhibitory Activity

The derivatives prepared in Examples 1-7 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The drugs were tested at a level of $10^{-4}$ M to determine the degree of inhibition of enzyme activity relative to untreated controls.

| Derivative Example | Degree of Inhibition at $10^{-4}$ Molar |
|---|---|
| 1 | 81% |
| 2 | 91% * |
| 3 | 91% |
| 4 | 94% * |
| 5 | 94% * |
| 6 | 65% |
| 7 | 100% |

*Average of two tests

Inhibition of Sorbitol Accumulation

Some of the Examples of derivatives prepared above were also tested for their ability to reduce or inhibit sorbitol accumulation in the sciatic nerve of streptozotocinized (i.e., diabetic) rats essentially by the procedure described in U.S. Pat. No. 3,821,383. In the present study, the amount of sorbitol accumulation in the sciatic nerves was measured 27 hours after induction of diabetes. The compounds were administered orally at the dose level indicated at 4, 8 and 24 hours following the administration of streptozotocin. The results obtained in this manner are presented in terms of percent inhibition (%) afforded by the test compound compared to the control where no compound was administered (i.e., the untreated animal where sorbitol levels normally rise from approximately 50-100 mM/g tissue to as high as 400 mM/g tissue in the 27-hour test period).

| Derivative Example | % Inhibition at Dose (mg./kg. t.i.d.) |
|---|---|
| 1 | 21% at 25 * |
| 2 | 9% at 25 |
| 3 | 11% at 25 |
| 4 | not tested |
| 5 | 4% at 25 * |
| 6 | not tested |
| 7 | 1% at 25 |

* Average of two tests

We claim:

1. A pharmaceutical preparation useful for prophylactic or remedial treatment of diabetic cataracts, retinopathy, nephropathy or neuropathy in a diabetic patient, which comprises:
a pharmaceutical carrier and a therapeutic amount of a coumarin carboxylic acid derivative selected from the group consisting of

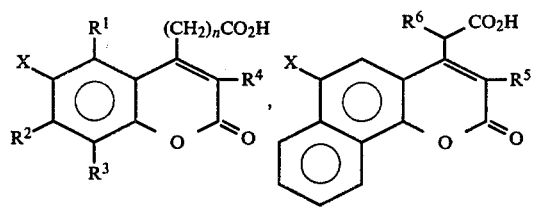

Formula I    Formula II and the pharmaceutically acceptable salts thereof, wherein
$R^1$, $R^2$, $R^3$, $R^4$, $R^5$ and $R^6$ are independently selected from H or $CH_3$;
X is H, $CH_3$, F or Cl; and
n is 0 or 1; provided that when $R^1$ is $CH_3$, $R^2$ or $R^3$ is $CH_3$.

2. A preparation of claim 1 containing the derivative of Formula I wherein $R^1$ and $R^3$ are H; $R^2$, $R^4$ and X are $CH_3$; and n is 1.

3. A preparation of claim 1 containing the derivative of Formula I wherein X, $R^3$ and $R^4$ are H; $R^1$ and $R^2$ are $CH_3$; and n is 1.

4. A preparation of claim 1 containing the derivative of Formula I wherein $R^1$, $R^3$, $R^4$ and X are H; $R^2$ is $CH_3$; and n is 1.

5. A preparation of claim 1 containing the derivative of Formula I wherein $R^1$, $R^3$ and $R^4$ are H; $R^2$ and X are $CH_3$; and n is 1.

6. A preparation of claim 1 containing the derivative of Formula I wherein $R^1$, $R^2$ and $R^4$ are H; $R^3$ is $CH_3$; X is Cl; and n is 0.

7. A preparation of claim 1 containing the derivative of Formula II wherein $R^5$ and $R^6$ are H; and X is Cl.

8. A preparation of claim 1 containing a mixture of the derivatives of Formula II wherein $R^5$ is H; $R^6$ is $CH_3$; and X is Cl and wherein $R^6$ is H; $R^5$ is $CH_3$; and X is Cl.

9. A method of prophylactically or remedially treating diabetic cataracts, retinopathy, nephropathy or neuropathy in a diabetic patient, which comprises:
administering to the patient in a form suitable for oral, intravenous, intramuscular, subcutaneous, topical or ophthalmic dosage, a therapeutic amount of a derivative of claim 1.

* * * * *